United States Patent [19]

Frank et al.

[11] Patent Number: 5,434,171
[45] Date of Patent: Jul. 18, 1995

[54] PREPARATION OF 3,4,4-TRISUBSTITUTED-PIPERIDINYL-N-ALKYLCARBOXYLATES AND INTERMEDIATES

[75] Inventors: Scott A. Frank, Lebanon; Douglas E. Prather, Brownsburg; Jeffrey A. Ward; John A. Werner, both of Indianapolis, all of Ind.

[73] Assignee: Eli Lilly and Company, Indianapolis, Ind.

[21] Appl. No.: 164,074

[22] Filed: Dec. 8, 1993

[51] Int. Cl.⁶ .................. A61K 31/445; C07D 211/32
[52] U.S. Cl. .................... 514/331; 514/317; 546/236; 546/237; 546/238; 546/239; 546/240
[58] Field of Search ............... 546/236, 237, 238, 239, 546/240; 514/317, 331

[56] References Cited

U.S. PATENT DOCUMENTS 5,136,040  8/1992  Werner ............... 546/218
5,250,542 10/1993  Cantrell et al. ............ 514/315

FOREIGN PATENT DOCUMENTS 506478  9/1992  European Pat. Off. .

OTHER PUBLICATIONS

Berge et al "Pharmaceutical Salts" J. Pharm. Sci. 66 1–2 (1977).
Cheronis "Semimicro Experimental Organic Chemistry" De Gratt Publishing, pp. 31–34 (1958).

*Primary Examiner*—Ceila Chang
*Attorney, Agent, or Firm*—MaCharri Vorndran-Jones

[57] ABSTRACT

This invention relates to a process for preparing certain 3,4,4-trisubstituted-piperidinyl-N-alkylcarboxylates, intermediates, and congeners. Finally, the invention provides new 3,4,4-trisubstituted-piperidinyl-N-alkylcarboxylates with formulations and methods for using the compounds.

17 Claims, No Drawings

PREPARATION OF 3,4,4-TRISUBSTITUTED-PIPERIDINYL-N-ALKYL-CARBOXYLATES AND INTERMEDIATES

FIELD OF THE INVNETION

This invention relates to a process for preparing certain 3,4,4-trisubstituted-piperidinyl-N-alkylcarboxylates, new intermediates and their congeners. Finally, this invention provides stable crystalline compounds and formulations useful as peripheral opioid antagonists.

BACKGROUND OF THE INVENTION

A substantial body of evidence indicates that peripheral opioid peptides and their receptors have a major physiological role in the regulation of gut motility. Consequently, gastrointestinal disorders such as idiopathic constipation and irritable bowel syndrome may relate to a dysfunction of opioid receptor mediated control, and agents which act as antagonists for these receptors may benefit a patient suffering from such a dysfunction.

The N-substituted piperidines, prepared using the process and intermediates of this invention are useful as peripherally-selective opioid antagonists. One particularly desirable 3,4,4-trisubstituted-piperidinyl-N-alkylcarboxylate is (2S,3R,4R)([[2-[[4-(3-hydroxyphenyl)-3,4-dimethyl-1piperidinyl]methyl]-1-oxo-3-phenyl-propyl]amino]acetic acid (1).

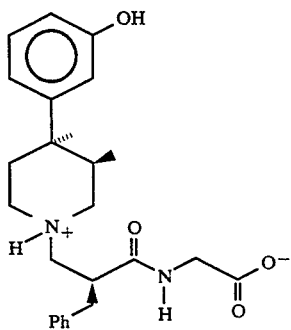

(1)

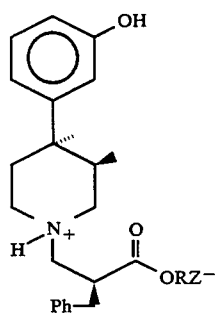

(2)

A generic process to prepare (αS,3R,4R)-4-(3-hydroxyphenyl)-3,4-dimethyl-α-(phenylmethyl)-1-piperidine propanoic acid ethyl ester (2), a useful intermediate for the preparation of 1, is known to the skilled artisan. Zimmerman describes this process in U.S. Pat. No. 5,250,542 (hereincorporated by reference). However, this process produces a mixture of stereoisomeric products which prevents its utilization in a practical commercial process. The preparation of the desired compound of Formula 1 requires a tedious chromato-graphic separation with only 13% yield for the isomer separation. Further, each intermediate is isolated as a "gum-like" product due to the presence of the undesired isomer. The "gum-like" product precludes purification of any intermediate without chromatography and is highly undesirable for commercial purposes.

The process of this invention now provides a synthetic route which will provide crystalline intermediates, without epimerization to facilitate the commercial preparation of 1 and $C_1$-$C_6$ alkyl esters thereof. Additionally, the process of this invention produces a crystalline solid of 1 and $C_1$-$C_6$ alkyl esters thereof in acceptable yields. Finally, the synthetic process of this invention includes crystalline intermediates to provide both enrichment and purification of the desired product.

This invention provides a highly desirable stable crystalline (2S,3R,4R)([[2-[[4-(3-hydroxyphenyl)-3,4-dimethyl-1 -piperidinyl]methyl]-1-oxo-3-phenylpropyl-]amino]acetic acid (1) which is the dihydrate.

The new crystalline intermediates and crystallization method are particularly important for the commercial development of the pharmaceutically active 3-4,4-trisubstituted-piperidinyl-N-alkylcarboxylates (18 and 18a infra.).

SUMMARY OF THE INVENTION

The presently claimed invention provides new crystalline salts of the Formula 2

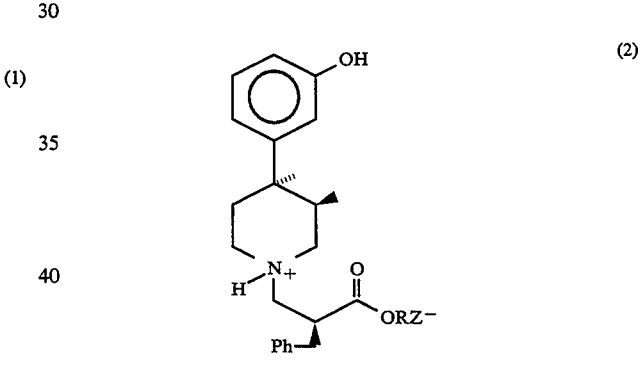

(2)

wherein R is $C_1$-$C_6$ alkyl; $z^-$ is selected from the group consisting of chloride, bromide, succinate, and (+)—dibenzoyltartrate; in acceptable yields.

The invention provides a process for preparing a crystalline monohydrate compound of Formula 3

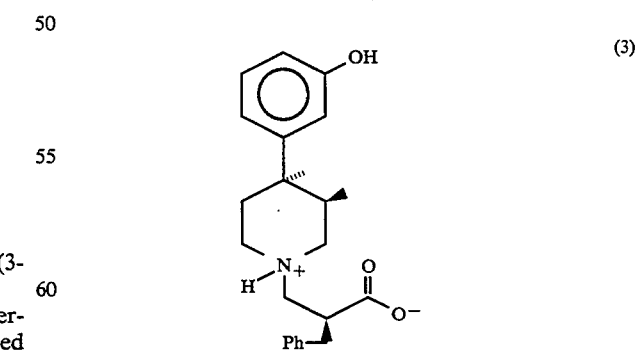

(3)

comprising the crystallization of 3 from a solvent comprised of about 50% to 75% lower alcohol and about 50% to 25% water (by weight).

Further, this invention provides crystalline compounds of the Formula 4

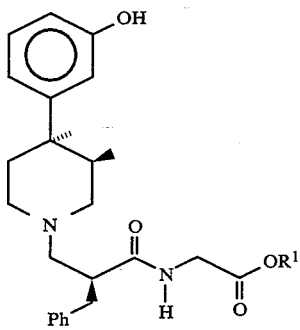

(4)

wherein $R^1$ is $C_1$-$C_6$ alkyl; the compound is a salt selected from the group consisting of hydrochloride and L-malate. The hydrochloride salt is a unique crystal form existing as the acetone monosolvate. The L-malate salts are also unique because their stoichiometry is dependent upon the solvent of crystallization. The stoichiometry may be either 1 molar equivalent each of L-malic acid and a compound of 4 or may be 3 molar equivalents of L-malic acid and 2 molar equivalents of a compound of 4. As used herein, the term "sesquimalate" refers to a 3:2 ratio of L-malic acid to compound 4.

Finally, this invention provides a crystalline dihydrate compound of the Formula 5

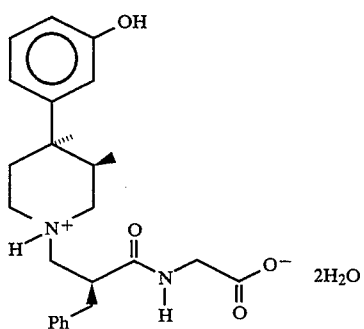

(5)

DETAILED DESCRIPTION OF THE INVENTION

The term "$C_1$-$C_6$ alkyl", as used herein, represents a branched or linear alkyl group having from one to six carbon atoms. Typical $C_1$-$C_6$ alkyl groups include methyl, ethyl, n-propyl, iso-propyl, butyl, iso-butyl, sec-butyl, tert-butyl, pentyl, hexyl, and the like. Other such terms represent straight chain or branched alkyl groups of the specified number of carbon atoms. For example, "$C_1$-$C_3$ alkyl" represents methyl, ethyl, n-propyl, and isopropyl.

The term "lower alcohol" refers to methanol, ethanol, 1-propanol, and 2-propanol.

The terms "inert atmosphere" and "inert conditions" refer to reaction conditions in which the mixture is covered with a layer of inert gas such as nitrogen or argon.

The term "substantially pure" is used herein to refer to at least about 90 mole percent of the desired absolute stereoisomer and/or polymorph. More preferably at least about 95 mole percent and most preferably at least about 98 mole percent of the desired absolute stereoisomer and/or polymorph is present.

Most preferably, the product of the process and compounds of the present invention are compounds existing as the 3R,4R-isomer as shown in Formula 3

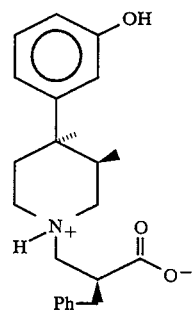

(3)

or the 3S,4S-isomer of Formula 6

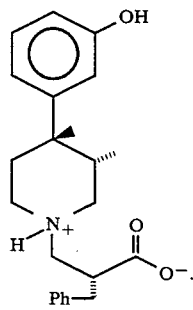

(6)

Further, the artisan will recognize that the benzyl substituent attaches at a chiral center. This invention encompasses both the (αS,3R,4R) and (αR,3S,4S) diastereomers. Especially preferred compounds of the present invention are those of Formulas 2, 3, 4, and 5 in which the configuration of substituents on the piperidine ring is 3R, 4R, and the carbon bearing the benzyl group is S. The artisan can choose appropriate reagents to prepare the opposite enantiomer.

The terms "R" and "S" are used herein as commonly used in organic chemistry to denote the specific configuration of a chiral center. See, Organic Chemistry, R.T.Morrison and R.N. Boyd, 4th ed., Allyn & Bacon, Inc., Boston (1983), pp 138–139 and The Vocabulary of OrGanic Chemistry, Orchin, et al., John Wiley and Sons Inc., p 126.

The term "hydrolysis" as used herein includes all appropriate known ester hydrolysis methods, including acidic, basic, and enzymatic processes. Preferred methods are described infra.

As used herein, the phrase "the crystallization of 3" refers to neutralizing the product of the hydrolysis reaction; Formula 7

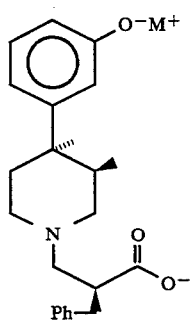

(7)

wherein M+ is sodium, lithium, or potassium, with the designated reagents and/or solvents and crystallizing using known techniques. The mixing may be accomplished using common agitation methods such as stirring, shaking, and the like. Further, the artisan recognizes that crystallization processes may include seeding, chilling, scratching the glass of the reaction vessel, and other such common techniques.

The starting materials for the present invention can be prepared by a variety of procedures well known to those of ordinary skill in the art. The 3-substituted-4-methyl-4-(3-hydroxy- or alkanoyloxyphenyl)piperidine derivatives employed as starting materials in the process of this invention can be prepared by the general procedure taught by Zimmerman in U.S. Pat. No. 4,115,400 (1978) and Zimmerman et al. in U.S. Pat. No. 4,891,379 (1990). U.S. Pat. Nos. 4,115,400 and 4,891,379 are incorporated herein by reference. The starting material for the synthesis of the compounds of the present invention, (3R,4R)-4-(3-hydroxyphenyl)-3,4-dimethylpiperidine, can be prepared by the procedure of Zimmerman in U.S. Pat. No. 5,250,542, herein incorporated by reference. The artisan should particularly note Example 1 of Zimmerman '542.

The starting material, 14, prepared as described in the art, can be used in the process of Scheme 1 (infra).

Scheme 1

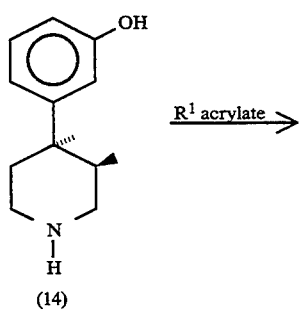

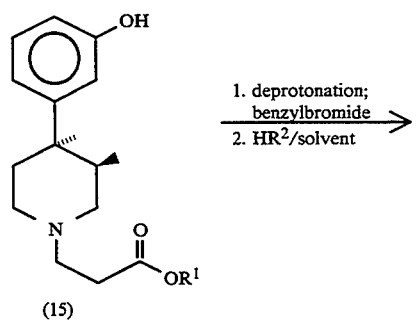

-continued
Scheme 1

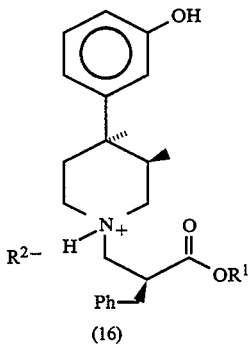

(16)

Wherein $R^1$ is defined supra. $R^2$ is chloride, bromide, (+)-dibenzoyltartrate, or succinate.

As illustrated in Scheme 1, compound 14 is contacted with an alkyl acrylate ($R^1$ acrylate) to form 15. $R^1$ is defined supra. Suitable solvents include methanol, tetrahydrofuran, ethanol, and others. The most preferred solvents are methanol and tetrahydrofuran.

Compound 15 is deprotonated and contacted with benzyl bromide. The deprotonation may be accomplished using an appropriate base. Examples of suitable base reagents include lithium diisopropylamide or lithium hexamethyldisilazide. Preferred solvents for the base reaction include tetrahydrofuran and 1,2-dimethoxyethane. The artisan will recognize that other solvents may be appropriate. When lithium diisopropylamide (LDA) is the base, it is most preferred that 2 equivalents of benzyl bromide are present. The alkylation product is a 1:1 mixture of the ($\alpha$S, 3R, 4R)-isomer and the ($\alpha$R, 3R, 4R)-isomer.

Crystalline compounds of formula 16 are new and unique. Only four specific salts of 16 were both stable crystalline salts and provided the desired diastereomeric enrichment. The following acids were each studied using four different solvent systems: HCl, HBr, (+)-dibenzoyl tartaric, succinic, (−)-di-p-toluoyl tartaric, (+)-di-p-toluoyl tartaric, (−)-dibenzoyl tartaric, (1R,3S)-(+)-camphoric, hippuric, benzoic, L-malic, D-malic, malonic, D-aspartic, (−)-tartaric, (+)-tartaric, (−)-mandelic, (+)-mandelic, L-ascorbic, maleic, sulfuric, acetic, phosphoric, citric, lactic, p-toluenesulfonic, D-arabascoric, and L-aspartic. Thus, over 110 crystallization studies yielded only four stable crystalline salts which provide enrichment! The enrichment and yield of the four stable crystalline salts is illustrated in Table I.

TABLE I

| Crystalline salts of the ester. | | | |
|---|---|---|---|
| Salt | Diast. Ratio | Yield | Solvent of Crystallization |
| hydrochloride | 88/12 | 39% | methanol |
| hydrobromide | 79/21 | 42% | methanol |
| (+)-DBTA[a] | 71/29 | 25% | ethyl acetate:acetone (1:1) |
| succinate | 83/17 | 25% | ethyl acetate:acetone (1:1) |

[a] (+)-dibenzoyl tartrate

As illustrated by Scheme 2 (infra), compound 16 is subject to hydrolysis to form compound 17. The artisan will recognize that compound 17 will be useful for preparing other useful compounds as illustrated by compound 18a. Compounds 18a are generically disclosed in U.S. Pat. No. 5,250,542 as being useful opioid antagonists. For the first time it is possible to prepare the pure absolute stereochemical isomers (18 and 18a) without tedious chromatographic separations using the new intermediates of this invention.

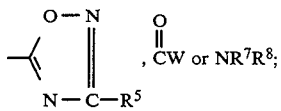

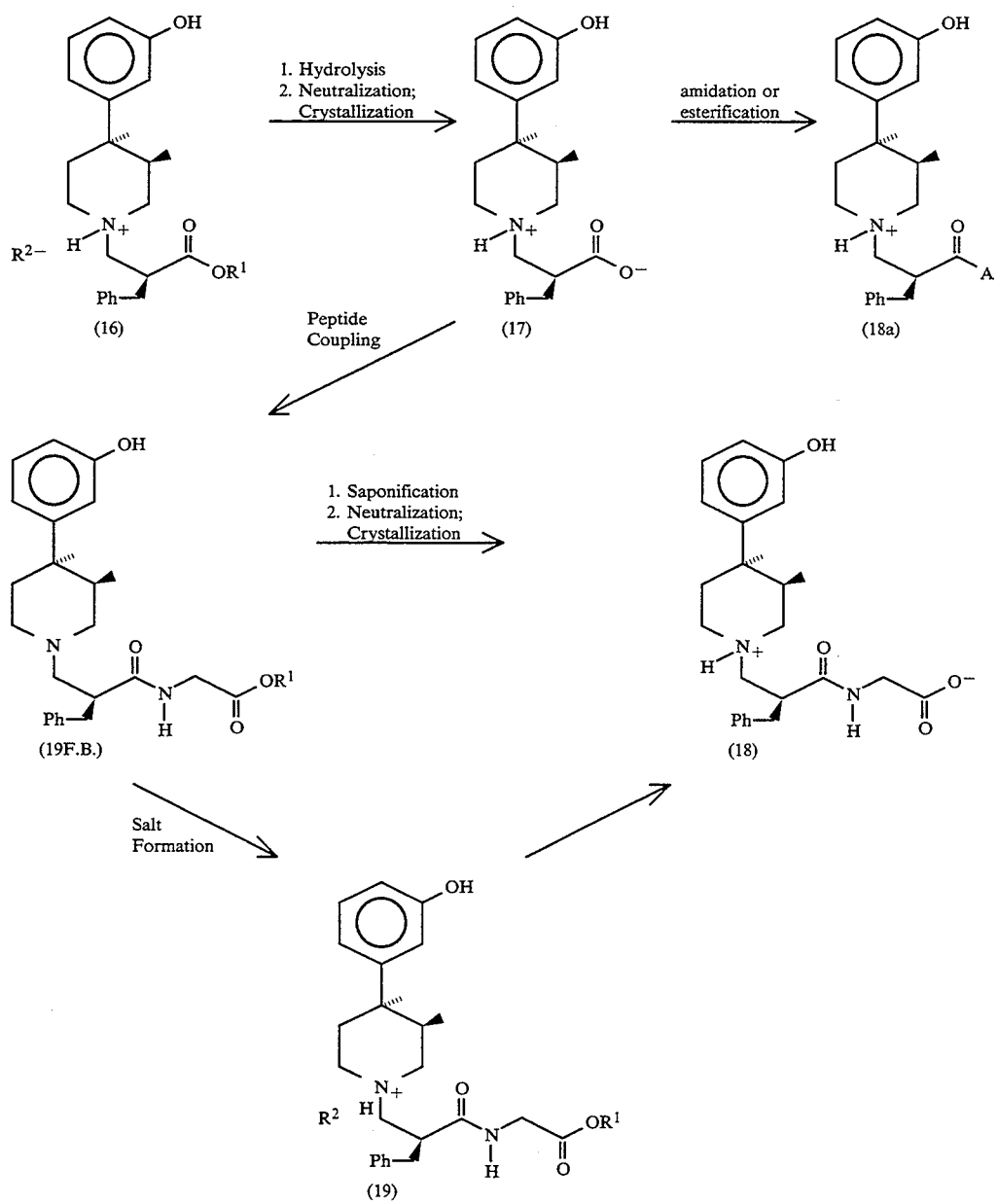

wherein $R^1$ and $R^2$ are as defined supra.

A is $OR^4$ or $NR^5R^6$; wherein:

$R^4$ is hydrogen, $C_1$–$C_{10}$ alkyl, $C_2$–$C_{10}$ alkenyl, cycloalkyl, $C_5$–$C_8$ cycloalkenyl, cycloalkyl-substituted $C_1$–$C_3$ alkyl, $C_5$–$C_8$ cycloalkenyl-substituted $C_1$–$C_3$ alkyl or phenyl-substituted $C_1$–$C_3$ alkyl;

$R^5$ is hydrogen or $C_1$–$C_3$ alkyl;

$R^6$ is hydrogen, $C_1$–$C_{10}$ alkyl, $C_3$–$C_{10}$ alkenyl, cycloalkyl, phenyl cycloalkyl-substituted $C_1$–$C_3$ alkyl, $C_5$–$C_8$ cycloalkenyl, $C_5$–$C_8$ cycloalkenyl-substituted $C_1$–$C_3$ alkyl, phenyl-substituted $C_1$–$C_3$ alkyl, or $(CH_2)$ q-B; or $R^5$ and $R^6$ together with N form a saturated non aromatic 4 to 6-membered heterocyclic ring;

$R^7$ iS hydrogen or $C_1$–$C_3$ alkyl;

$R^8$ is hydrogen, $C_1$–$C_{10}$ alkyl, $C_3$–$C_{10}$ alkenyl, cycloalkyl-substituted $C_1$–$C_3$ alkyl, cycloalkyl, $C_5$–$C_8$ cycloalkenyl, $C_5$–$C_8$ cycloalkenyl-substituted $C_1$–$C_3$ alkyl, phenyl or phenyl-substituted $C_1$–$C_3$ alkyl; or $R^7$ and $R^8$ together with N form a saturated non aromatic 4- to 6-membered heterocyclic ring;

w is $OR^9$, $NR^{10}R^{11}$, or OE;

$R^9$ is hydrogen, $C_1$–$C_{10}$ alkyl, $C_2$–$C_{10}$ alkenyl, cycloalkyl, $C_5$–$C_8$ cycloalkenyl, cycloalkyl-substituted $C_1$-$C_3$ alkyl, $C_5$-$C_8$ cycloalkenyl-substituted $C_1$-$C_3$ alkyl or phenyl-substituted $C_1$-$C_3$ alkyl;

$R^{10}$ is hydrogen or $C_1$-$C_3$ alkyl;

$R^{11}$ is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$ alkyl, phenyl-substituted $C_1$-$C_3$ alkyl, or

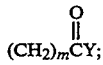

or $R^{10}$ and $R^{11}$ together with N form a saturated non aromatic 4- to 6-membered heterocyclic ring;

E is

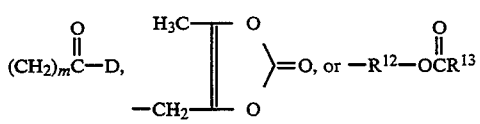

$R^{12}$ is $C_1$-$C_3$ alkyl substituted methylene, $R^{13}$ is $C_1$-$C_{10}$ alkyl;

D is $OR^{14}$ or $NR^{15}R^{16}$; wherein:

$R^{14}$ is hydrogen, $C_1$-$C_{10}$ alkyl, $C_2$-$C_{10}$ alkenyl, cycloalkyl, $C_5$-$C_8$ cycloalkenyl, cycloalkyl-substituted $C_1$-$C_3$ alkyl, or $C_5$-$C_8$ cycloalkenyl-substituted $C_1$-$C_3$ alkyl or phenyl-substituted $C_1$-$C_3$ alkyl;

$R^{15}$ is hydrogen, $C_1$-$C_{10}$ alkyl, $C_3$-$C_{10}$ alkenyl, phenyl, phenyl-substituted $C_1$-$C_3$ alkyl, cycloalkyl, $C_5$-$C_8$ cycloalkenyl, cycloalkyl-substituted $C_1$-$C_3$ alkyl or $C_5$-$C_8$ cycloalkenyl-substituted $C_1$-$C_3$ alkyl; and $R^{16}$ is hydrogen or $C_1$-$C_3$ alkyl; or $R^{15}$ and $R^{16}$ together with N form a saturated non aromatic 4- to 6-membered heterocyclic ring;

Y is $OR^{17}$ or $NR^{18}R^{19}$;

$R^{17}$ is hydrogen, $C_1$-$C_{10}$ alkyl, $C_2$-$C_{10}$ alkenyl, cyclocalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl, or phenyl-substituted $C_1$-$C_3$ alkyl;

$R^{18}$ is hydrogen or $C_1$-$C_3$ alkyl; and $R^{19}$ is is hydrogen, $C_1$-$C_{10}$ alkyl, $C_3$-$C_{10}$ alkenyl, phenyl, cycloalkyl, $C_5$-$C_8$ cycloalkenyl, cycloalkyl-substituted $C_1$-$C_3$ alkyl, $C_5$-$C_8$ cycloalkenyl-substituted $C_1$-$C_3$ alkyl, or phenyl-substituted $C_1$-$C_3$ alkyl; or $R^{18}$ and $R^{19}$ together with N form a saturated non aromatic 4- to 6-membered heterocyclic ring;

q is 1–4;

m is 1–4.

The "A" substituent is described in U.S. Pat. No. 5,250,542.

The hydrolysis reaction may be completed using known acidic hydrolysis methods. An example of one such acidic hydrolysis method is treatment with an aqueous acid in refluxing dioxane. More preferredly, the hydrolysis reaction is completed using saponification conditions to avoid epimerization. Examples of saponification reagents include lithium hydroxide, sodium hydroxide, potassium hydroxide, and the like.

The product of the hydrolysis reaction (the carboxylate salt) is adjusted to the isoelectric point of the amino acid using aqueous acid to provide the zwitterion 17. Crystallization of the monohydrate of 17 must be completed using 50% to 75% lower alcohol and 50% to 25% water.

Table I illustrates the critical dependence of the crystallization on the approximate 1:1 lower alcohol/water solvent. The term "gumball" refers to the coagulation of a sticky semi-solid product into an amorphous mass.

TABLE I

| Entry | % cosolvent | Acid Conc. | Yield | Comments |
|---|---|---|---|---|
| 1 | none | 12N HCl | 86% | gumball |
| 2 | none | 12N HCl | 88% | gumball |
| 3 | none | 12N HCl | 93% | gumball |
| 4 | none | 1N HCl | 90% | gumball |
| 5 | none | 6N HCl | 91% | gumball |
| 6 | none | 1M H₃PO₄ | 93% | gumball |
| 7 | none | 6M H₃PO₄ | 97% | gumball |
| 8 | none | 1M AcOH | 99% | gumball |
| 9 | 6 MeOH | 12N HCl | 88% | gumball |
| 10 | 12 MeOH | 12N HCl | 87% | gumball |
| 11 | 25 MeOH | 12N HCl | 82% | gumball |
| 12 | 25 MeOH | 12N HCl | 90% | gumball |
| 13 | 50 MeOH | 12N HCl | 58%* | gumball |
| 14 | 50 MeOH | 12N HCl | 82% | crystal |
| 15 | 50 MeOH | 12N HCl | 90%** | crystal |
| 16 | 50 MeOH | 12N HCl | 95.9%** | crystal |
| 17 | 50 i-Pr | 12N HCl | 73% | crystal |
| 18 | 50 ACN | 12N HCl | 23% | crystal |

ACN refers to acetonitrile; i-Pr refers to isopropyl alcohol. * Due to reaction concentration of 10mL solvent/g of 16 ** Yield increase is due to removal of methanol by distillation after crystallization has occurred.

As illustrated in Scheme 2, the product 17 can be used directly in the amidation/esterification step. When amidation is desired, the amino acid should be selected to produce the desired compounds of formula 18 or 18a. The amino acid is contacted with a glycine ester in a solvent such as dimethylformamide or tetrahydrofuran. Dicyclohexylcarbodiimide is used as the coupling reagent. N-hydroxybenzotriazole is added as the auxiliary nucleophile. The coupling reaction may be run under inert conditions. More preferably, the peptide coupling reaction uses tetrahydrofuran as the solvent. The artisan will recognize that other peptide coupling methods will also be effective.

Alternatively, a crystalline salt of compound 19F.B. (free base) can be prepared as illustrated in Scheme 2 supra. Crystallization studies were conducted using 17 different acids with three solvents; ethyl acetate, acetone, and ethanol. Of those 51 experiments, only the L-malic and hydrochloric acids yielded crystalline salts stable at 25 °C.

The crystalline hydrochloride salt is obtained by contacting 19F.B. with anhydrous HCl in acetone. Capillary gas chromatographic analysis indicates that the salt is produced as the monosolvate of acetone. This unique monosolvate crystal form allows compound 19 to be isolated in substantially pure form. Contacting 19F.B. with anhydrous HCl in other solvents produces an amorphous solid without substantial purification.

Applicants have discovered that the L-malic acid salt can be prepared as a stable crystalline solid having two ratios of 19F.B. to L-malic acid, depending on the solvent of crystallization. When the crystallization is completed in solvents such as methyl ethyl ketone, acetone, acetone/t-butyl methyl ether, or acetone/heptane the expected stoichiometry of 1:1 19F.B. to L-malic acid is found. However, when the crystallization is carried out in solvent systems of acetone/ethyl acetate, acetone/toluene, or ethanol/toluene the crystalline salt is afforded with the unique stoichiometry of a 3:2 ratio of L-malic acid to 19F.B.(sesquimalate) This result is particularly unexpected when the sesquimalate is obtained even when a 1:1 ratio of malic acid and 19F.B. are combined in certain solvents. Indeed, when equimole amounts of L-malic acid and 19F.B. are combined in a sesquimalate-forming solvent or solvent system, the sesquimalate is the sole salt formed in about 67% yield, with the mass balance being 19F.B. in the mother liquor. Certainly, the artisan would expect the ratio to be 1:1. Moreover, crystallization of a sesquimalate salt in a "non-sesquimalate-forming" solvent of solvent systems forms only the crystalline monomalate salt in nearly quantitative yield, with the excess L-malic acid remaining in the mother liquor.

Crystallization of the sesquimalate salt provides a product of pharmaceutically acceptable purity in a high yield with crystals of highly consistent crystal form and size. The hydrochloride and sesquimalate salts can be used as prodrug entities since the isobutyl ester is readily cleaved in vivo.

The acids which did not form crystalline salts stable at 25° C. include HBr, $H_2SO_4$, hippuric, d-tartaric, l-tartaric, malonic, succinic, acetic, arabascorbic, ascorbic, citric, benzoic, lactic, (S)-(+)-mandelic, and (R)-(−)-mandelic acids. Thus, demonstrating the surprising and unique nature of the L-malic and HCl salts.

The product of the amidation/esterification reaction or salt forms thereof, can be hydrolyzed using standard methods. Preferably, basic hydrolysis methods are used. Preferred saponification reagents include sodium hydroxide, potassium hydroxide, lithium hydroxide, and the like. Most preferably, the saponification step is completed using sodium hydroxide and a solvent. Particularly preferred solvents are (1:1) methanol:water and (2:1) ethanol:water. The reaction is quenched using an acid such as hydrochloric acid. After neutralization (pH=6), the crystalline solid dihydrate product 18 is directly isolated by filtration. The isolated product 18 is of pharmaceutically acceptable purity without subsequent purification steps.

The new dihydrate 18 is particularly desirable because the compound is a stable crystalline solid, is of consistent crystal form and particle size to provide reproducible dissolution rates, and is of pharmaceutically desirable quality.

The compounds of Formula 5 and 4 supra. are useful in blocking peripheral opioid receptors and preventing peripheral opiate induced side effects. These side effects are induced by administration of an opiate such as morphine to a mammal. The opiate induced side effects can include constipation, nausea, and vomiting. Thus, the compounds of this invention are useful for treating one or more opiate induced side effects. These compounds can also be useful in the treatment of irritable bowel syndrome, non-ulcer dyspepsia, and idiopathic constipation. These compounds do not substantially pass through the blood-brain barrier and therefore do not mitigate the opioid's effect on central (brain and spinal cord) opioid receptors. Consequently, these characteristics indicate that the compounds will also be substantially free of other centrally mediated effects.

In order to determine in vivo opioid receptor antagonism, the mouse writhing analgesis test was used. Test compounds were measured for their ability to block morphineinduced analgesia.

Five CF-1 male mice (Charles River, Portage, MI), weighing approximately 20 g after being fasted overnight, were observed simultaneously for the writhing response. The writhing response was defined as a contraction of the abdominal musculature, followed by the extension of the hind limbs, and was induced by the intraperitoneal administration of 0.6% acetic acid in a volume of 1 mL/100 g of body weight. The observation period was 10 minutes in duration, beginning 5 minutes after injection of acetic acid. The percent inhibition of writhing was calculated from the average number of writhes in the control (non-drug) group. The $ED_{50}$ was defined as the dose of agonist that inhibited mean writhing by 50%. The $AD_{50}$ was defined as the dose of antagonist that reduced the inhibition of writhing produced by a 1.25 mg/kg dose of morphine sulfate to 50%. Each mouse was used only once. All drugs were administered subcutaneously (1 mL/100 g bwt) 20 minutes before the injection of acetic acid.

Determinations of peripheral opioid activity were conducted. Mice were maintained on 0.01 M. saccharin water with 1 g/L morphine sulfate for a minimum of 10 days with the mice averaging over 3.0 g of water per mouse per day for at least 3 days. The morphine water was removed 45 minutes prior to injection with the proposed opioid antagonist. After administration of the opioid antagonist, the mice were placed in plastic cylinders with white paper towels for a floor.

The mice were monitored visually for 30 minutes post-injection for the presence of jumping and of diarrhea. Jumping was scored as positive if at least one jump occurred in 30 minutes. Diarrhea was scored as positive when feces were moist enough to stain the white paper at the base of the cylinder. After 30 minutes of testing, the mice were returned to their original cages, put back on morphine water, and not tested again for 48 hours. Lower doses of the antagonist compounds were tested until threshold doses for diarrhea were determined. Diarrhea is a peripherally mediated sign of precipitated opiate abstinence.

The extent of the effect on peripheral activity compared to central activity of the present compounds can be determined by comparing the $AD_{50}$ for the mouse writhing test with the $ED_{50}$ for the mouse diarrhea test. The higher the ratio, the greater relative antagonism of the peripheral opioid receptors by a particular compound.

The $AD_{50}$ values for the compounds of this invention are over 8 mg/kg, while the $ED_{50}$ values are under 1.

Further, the compounds of Formulas 5 and 4 supra. have been found to display excellent activity in an opioid receptor binding assay which measures the affinity of the compounds to bind mu receptors. This assay was conducted by the following procedure.

Male Sprague Dawley rats were sacrificed via decapitation and the brains were removed. The brain tissue with the cerebellum removed was homogenized in a Teflon and glass tissue homogenizer. A supernatant I, pellet IV, fraction was frozen in a nitrogen freezer at 1.33 g/mL concentration and stored for not longer than five weeks prior to use.

increasing concentrations of experimental compound, (0.1 to 1000 nanomolar (nM)), Krebs-Hepes buffer pH 7.4, and tritiated naloxone (0.5 nM) ($^3H$ ligand) were combined in polystyrene tubes at room temperature. The reaction was initiated by the addition of the resuspended tissue which had been preincubated at 37° C. for 20 minutes. The reaction mixture was incubated in a 37° C. water bath for 20 minutes. The reaction was terminated by rapid filtration, (Brandel cell harvester), through Whatman GF/B glass filters that had been presoaked in Krebs-Hepes buffer pH 7.4. The filters were then washed 2 times with 5 mL of ice cold Krebs-Hepes buffer of pH 7.4. Washed filters were placed in scintillation vials and 10 mL, (Brandel), was added and samples were counted in a Searle D-300 beta counter. The incubation time for the reaction mixture was 20 minutes at 37° C. The $K_i$ and $K_D$ values were calculated using standard methods.

The compounds of this invention exhibit highly desirable activity profiles. The value for percent displacement by the test compounds at 10 nM concentration was over 75% and over 80% at 100 nM. This is particularly desirable in light of the $AD_{50}$ and $ED_{50}$ values (supra). The results indicate that the compounds of this invention have favorable activity profiles for use in the treatment of irritable bowel syndrome and conditions related to the binding of mu receptors.

While it is possible to administer a compound of this invention directly without any formulation, the compounds are preferably employed in the form of a pharmaceutical formulation comprising a pharmaceutically acceptable excipient and at least one compound of the invention. The effective dosage range for the compounds of this invention is broad. Thus, such compositions contain from about 0.1 percent by weight to about 90.0 percent by weight of a presently claimed compound. As such, the present invention also provides pharmaceutical formulations comprising a compound of this invention and a pharmaceutically acceptable excipient therefor.

In making the formulations of the present of the present invention, the acnive ingredient is usually mixed with an excipient which can be a carrier, or a diluent, or be diluted by a carrier, or enclosed within a carrier which may be in the form of a capsule, sachet, paper or other container. When the carrier serves as a diluent, it can be a solid, semi-solid, or liquid material which acts as a vehicle, excipient, or medium for the active ingredient. Thus, the formulation can be in the form of tablets, pills, powders, lozenges, sachets, cachets, elixirs, emulsions, solutions, syrups, suspensions, aerosols (as a solid or in a liquid medium), suppository, and soft and hard gelatin capsules.

The compounds of this invention may be delivered transdermally, if desired. Transdermal permeation enhancers and delivery systems, including patches and the like are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferably, a compound of this invention is admixed with permeation enhancers including, but not limited to, propylene glycol, polyethylene glycol, monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules. The compounds of this invention may be prepared as microparticles or microspheres. Microparticles may be prepared using polyglycolide, polylactide, or other polymers to facilitate sustained release of the active compound or prodrug.

The compositions are preferably formulated in a unit dosage form, each dosage containing from about 1 to about 500 mg, more usually about 5 to about 300 mg, of the active ingredient. Another preferred range is about 0.5 mg to about 60 mg of the active ingredient per unit dosage form. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

The artisan will recognize that the compounds of this invention may be formulated with other known medicaments. The co-formulation may provide a synergistic therapeutic effect. For example, an antacid can be formulated with the compounds of this invention to provide a desired gastrointestinal effect.

In order to more fully illustrate the operation of this invention, the following formulation examples are provided. The examples are illustrative only, and are not intended to limit the scope of the invention. The formulations may employ as active compounds any of the compounds of the present invention.

FORMULATION 1

Hard gelatin capsules are prepared using the following ingredients:

|  | Amount Per Capsule | Concentration by Weight (percent) |
|---|---|---|
| (2S,3R,4R)[[2-[[4-(3-hydroxyphenyl)-3,4-dimethyl-1-piperidinyl] methyl]-1-oxo-3-phenylpropyl]amino]acetic acid methyl ester, hydrochloride | 250 mg | 55.0 |
| Starch dried | 200 mg | 43.0 |
| Magnesium stearate | 10 mg | 2.0 |
|  | 460 mg | 100.0 |

The above ingredients are mixed and filled into hard gelatin capsules in 460 mg quantities.

Formulation 2

Capsules each containing 20 mg of medicament are made as follows:

|  | Amount Per Capsule | Concentration by Weight (percent) |
|---|---|---|
| (2S,3R,4R)[[2-[[4-(3-hydroxyphenyl)-3,4-dimethyl-1-piperidinyl]-methyl]-1-oxo-3-phenylpropyl]amino]acetic acid ethyl ester, hydrochloride monohydrate | 20 mg | 10 |

-continued

|  | Amount Per Capsule | Concentration by Weight (percent) |
|---|---|---|
| Starch | 89 mg | 44.5 |
| Microcrystalline cellulose | 89 mg | 44.5 |
| Magnesium stearate | 2 mg | 1.0 |
|  | 200 mg | 100.0 |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Amount Per Capsule | Concentration by Weight (percent) |
|---|---|---|
| (2S,3R,4R)[[2-[[4-(3-hydroxyphenyl)-3,4-dimethyl-1-piperidinyl]-methyl]-1-oxo-3-phenyl-propyl]amino]acetic acid, dihydrate | 100 mg | 30.0 |
| polyoxyethylene sorbitan monooleate | 50 mg | 0.02 |
| starch powder | 250 mg | 69.98 |
|  | 350 mg | 100.0 |

The above ingredients are thoroughly mixed and placed in an empty gelatin capsule.

Formulation 4

Tablets containing 10 mg of active ingredient are made as follows:

|  | Amount Per Tablet | Concentration by Weight (percent) |
|---|---|---|
| (2S,3R,4R)[[2-[[4-(3-hydroxyphenyl)-3,4-dimethyl-1-piperidinyl] methyl]-1-oxo-3-phenyl-propyl]amino]acetic acid, ethyl ester, sesquimalate | 10 mg | 10.0 |
| Starch | 45 mg | 45.0 |
| Microcrystalline Cellulose | 35 mg | 35.0 |
| Polyvinylpyrrolidone (as 10% solution in water) | 4 mg | 4.0 |
| Sodium Carboxymethyl Starch | 4.5 mg | 4.5 |
| Magnesium Stearate | 0.5 mg | 0.5 |
| Talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate, and talc, previously passed through a No. 60 mesh U.S. sieve, are then added to the granule which, after mixing, is compressed on a tablet machine to yield a tablet weighing 100 mg.

Formulation 5

A tablet formulation may be prepared using the ingredients below:

|  | Amount Per Tablet | Concentration by Weight (percent) |
|---|---|---|
| (2S,3R,4R)[[2-[[4-(3-hydroxyphenyl)-3,4-dimethyl-1-piperidinyl]-methyl]-1-oxo-3-phenyl-propyl]amino]acetic acid, dihydrate | 250 mg | 38.0 |
| Microcrystalline cellulose | 400 mg | 60.0 |
| Silicon Dioxide fumed | 10 mg | 1.5 |
| Stearic Acid | 5 mg | 0.5 |
|  | 665 mg | 100.0 |

The components are blended and compressed to form tablets weighing 665 mg.

Formulation 6

A hard gelatin capsule may be prepared using the following ingredients:

|  | Amount Per Capsule | Concentration by Weight (percent) |
|---|---|---|
| (2S,3R,4R)[[2-[[4-(3-hydroxyphenyl)-3,4-dimethyl-1-piperidinyl]-methyl]-1-oxo-3-phenyl-propyl]amino]acetic acid, dihydrate | 66 mg | 18 |
| Polyethylene Glycol | 300 mg | 82 |
|  | 366 mg | 100 |

All solid ingredients are sieved. Polyethylene Glycol is melted and maintained in a molten state. The medicament is incorporated into the molten vehicle. The molten homogeneous suspension is filled into hard gelatin capsules to the appropriate weight or volume using suitable oil paste filling equipment.

Capsules containing 6 mg of active substance may be prepared exactly as describe above; however, the amount of dihydrate compound should be reduced to 6.6 mg per capsule. Capsules containing 0.6 mg of active substance may be prepared as described above; however, the amount of dihydrate should be reduced to 0.66 mg with 200 mg Polyethylene Glycol per capsule.

The intermediates and processes of the present invention are useful for preparing compounds having beneficial peripheral opioid antagonist activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

A) The crystalline compound 2 is the methyl ester.ester.

B) The crystalline compound 2 is ($\alpha$S,3R,4R)-3-[[4-(3-hydroxyphenyl)-3,4-dimethyl-$\alpha$-(phenylmethyl)-1-piperidine propanoic acid, methyl ester hydrochloride.

C) The crystalline compound 2 is the ethyl ester.

D) The crystalline compound 2 is the HBr salt.

E) The lower alcohol is methanol.

F) The lower alcohol:water ratio is 50-60% lower alcohol and 50-40% water.

G) $R^1$ is $C_1$-$C_4$ alkyl.

H) The crystalline compounds of Formula 4 are the sesquimalate salt.

I) The crystalline compounds of Formula 4 are the hydrochloride acetone monosolvate form.

J) The substantially pure dihydrate of Formula 5 is 97% or more 2S, 3R, 4R dihydrate.

K) A pharmaceutical formulation comprising a dihydrate compound of Formula 5 and one or more pharmaceutically acceptable excipients.

L) A pharmaceutical formulation comprising a sesquimalate salt of a compound of Formula 4.

M) A method of using a compound of Formula 5 to treat irritable bowel syndrome.

N) A method of using one or more compounds of Formula 4 to treat irritable bowel syndrome.

O) A method for binding a mu receptor comprising administering an effective amount of a compound of Formula 5.

P) A method for binding a mu receptor comprising administering an effective amount of one or more compounds of Formula 4.

The preferred embodiments of this invention are represented by A-P.

The following examples are provided for purposes of illustration and are not to be construed as limiting the scope of the claimed invention.

The concentration of reactants is not critical for the invention. The art worker can alter the concentration of the reactants to achieve the desired rate of reaction and product yield.

The length of time for carrying out the processes described is not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

As used in the instant examples, the following terms have the meanings indicated. "HOBt" refers to 1-hydroxybenzotriazole hydrate. "THF" refers to tetrahydrofuran. "DMF" refers to dimethylformamide. "TEA" refers to triethylamine. "DCC" refers to dicyclohexylcarbodiimide.

PREPARATION 1

(3R,4R)-4-(3-hydroxyphenyl)-3,4-dimethyl-1-piperidinepropanoic acid methyl ester A round bottom flask was charged with THF (1000 mL) and (+)-3-(3,4-dimethyl-4-piperidinyl)phenol (70.46 g, 0.343 mol). The suspension was heated to 40°-45° C. and methyl acrylate (46.4 mL, 0.515 mol, 1.5 equiv) was added over three minutes. No change in temperature was observed.

The reaction was stirred at 45° C. and the progress monitored by HPLC. The reaction mixture remained cloudy. After four hours, the reaction mixture was cooled to room temperature and filtered through diatomaceous earth. The solvent and excess methyl acrylate were removed by concentration of the solution via rotary evaporation at 40° C. to a net weight of 120 g. The crude product was redissolved in THF (180 g) to give a 33.3 wt % solution for use in the process of Example 2.

Quantitative yield by HPLC. $[\alpha]s(20,D)$ 75.3° (C 1.01, MeOH), $[\alpha]^{20}_{365}$ 245.6° (c 1.01, MeOH). IR (CHCl$_3$): 3600, 3600-3100, 1732, 1440 cm$^{-1}$. $^1$H-NMR (CDCl$_3$): $\delta$0.72 (d, 3H, J=7.0 Hz), 1.30 (s, 3H), 1.59 (br d, 1H), 1.90-2.03 (m, 1H), 2.25-2.50 (m, 2H), 2.50-2.90 (m, 7H), 3.66 (s, 3H), 6.63 (dd, 1H, J=7.8, 2.0 Hz), 6.73 (br s, 1H), 6.81 (d, 1H, J=7.8 Hz), 7.15 (t, 1H, J=8.0 Hz). $^{13}$C-NMR (CDCl$_3$): $\delta$16.1, 27.4, 30.8, 32.0, 38.4, 38.9, 49.9, 51.7, 53.9, 55.7, 55.8, 112.5, 112.6, 113.0, 113.2, 117.6, 117.7, 129.2, 151.6, 156.1, 173.4. UV (EtOH): $\lambda_{max}$ 274 nm, $\epsilon$2028; 202 nm, $\epsilon$17350. MS (FAB): m/z 292 (100%, M+1), 292 (18%, M+), 218 (65%).

PREPARATION 2

Isobutyl glycine, p-toluenesulfonic acid salt

A round bottom flask was charged with toluene (600 mL), glycine (22.53 g, 0.30 mol), p-toluenesulfonic acid monohydrate (62.76 g, 0.33 mol, 1.1 equiv) and isobutyl alcohol (60 mL, 0.65 mol, 2.17 equiv). The heterogeneous reaction mixture was stirred and heated to reflux with a heating mantle to azeotropically remove the water as it was formed. After two hours the reaction mixture was homogeneous. After an additional 1.5 hours the reaction mixture was cooled to 50° C. and concentrated via rotary evaporation at 60° C. to a net weight of 135 g.

The residue (homogeneous oil) was dissolved in ethyl acetate (450 mL) while it was still warm and the solution transferred to a 3-necked round bottom flask equipped with a mechanical stirrer and a reflux condenser. Hexane (450 mL) was added to the solution with stirring at room temperature. The slurry was then heated to reflux to redissolve the solid and the solution allowed to cool slowly, with stirring. The solution was seeded at 38° C. to initiate crystallization. After cooling to room temperature the mixture was cooled to 5° C. and stirred for an additional hour. The product was isolated by filtration through a frittedglass funnel, air-dried for ½ hours and then dried overnight in a vacuum oven (40° C., 5 mm Hg). A total of 89.1 g (97.9%) of a white crystalline solid was obtained.

mp=77.2-79.6° C. pKa (67% aq. DMF)=7.68. IR (CHCl$_3$): 3300-2600, 3018, 2970, 1752, 1213, 1125, 1033, 1011 cm$^{-1}$. $^1$H-NMR (300 MHz, CDCl$_3$) $\delta$0.82 (d, 6 H, J=6.9), 1.79 (sept., 1 H, J=6.8), 2.33 (s, 3 H), 3.66 (br s, 2 H), 3.78 (d, 2 H, J=6.6), 7.10 (d, 2H, J=8.1), 7.72 (d, 2 H, J=8.2), 8.03 (br s, 3 H). $^{13}$C-NMR (75.4 MHz, CDCl$_3$) $\delta$18.9, 21.3, 27.4, 40.3, 72.0, 126.1, 128.9, 140.3, 141.4, 167.5.

Analysis for $C_{13}H_{21}NO_5S$:

Calculated: C, 51.47; H, 6.98; N, 4.62; S, 10.57.

Found: C, 51.74; H, 6.77; N, 4.76; S, 10.73.

EXAMPLE 1

(2S, 3R, 4R)[[2-[[4-(3-hydroxyphenyl)-3,4-dimethyl-1-piperidinyl]methyl]-1-oxo-3-phenylpropyl]-amino]acetic acid 2-methylpropyl ester A round bottomed flask was charged with (αS,3R,4R)-4-(3-hydroxyphenyl)-3,4-dimethyl-α-(phenylmethyl)-1-piperidine propanoic acid (20.11 g, 0.0522 mol, 1 equiv), a compound of Preparation 2 (17.60 g, 0.058 mol, 1.11 equiv), hydroxybenzotriazole monohydrate (7.83 g, 0.058 mol, 1.11 equiv) and dry tetrahydrofuran (144 mL). Triethylamine (8.08 mL, 0.058 mol, 1.11 equiv) was added to the mixture, followed by dicyclohexylcarbodiimide (11.97 g, 0.058 mol, 1.11 equiv) dissolved in tetrahydrofuran (60 mL). The mixture was stirred at 25° C. under nitrogen for two days. The completion of the reaction was monitored using HPLC. The slurry was cooled at 0° C. for two hours and then filtered. The filtrate was then evaporated to near dryness under reduced pressure (10 Torr) at 40° C. The oil was taken up in 250 mL of ethyl acetate. The organic layer was washed with 250 mL of a 0.5 M, pH 9.8 $CO_3^{-2}/HCO_3^{-1}$ buffer solution. The pH was adjusted to 9.5–9.8. The organic solution was washed with 250 mL of saturated brine. The organic layer was dried over $Na_2SO_4$, cooled with stirring to −20° C. and allowed to stand, unstirred at −20° C. overnight (16 hr). The precipitated DCU was removed by filtration. The ethyl acetate was evaporated under reduced pressure (10 Torr) to yield 25.0 g (95%) of an amorphous solid.

IR ($CHCl_3$) 2897, 1740, 1659 $cm^{-1}$; $^1H$ NMR (300 MHz, $CDCl_3$) δ8.94 (dd, 1H, J=2.0 Hz), 8.40 (bs, 1H), 7.20–6.93(m, 4H), 6.60–6.50 (m, 3H), 4.04, 3.95 (m, 2H), 3.80–3.65 (m, 2H), 3.16 (dd, 1H, J=13.8 Hz, J=4.4 Hz), 2.69 (bd, 1H, J=10.2 Hz), 2.63–2.41 (m, 4H), 2.40–2.15 (m, 4H), 1.84–1.71 (m, 2H), 1.42 (bd, 1H, J=12.4 Hz), 1.10 (s, 3H), 0.77 (d, 6H, J =6.9 Hz), 0.57 (d, 3H, J=6.9 Hz), $^1H$ NMR (300 MHz, DMSO-$d_6$): δ9.17 (bs, 1H), 8.40 (bt, 1H, J=2.0 Hz), 7.26–7.14 (m, 4H), 7.04 (t, 1H, J=7.8 Hz), 6.63 (m, 2H), 6.52 (d, 1H, J=8.1 Hz ), 3.81–3.79 (m, 4H), 2.90–2.43 (m, 6H), 2.37 (d, 1H, J=12.4 Hz), 2.33–2.03 (m, 3H), 1.95–1.65 (m, 2H), 1.43 (d, 1H, J=12.4 Hz), 1.17 (s, 3H), 0.85 (d, 6H, J=6.7 Hz) 0.65 (d, 3H, J=6.8 Hz); $^{13}C$ NMR (75.4 MHz, DMSO-$d_6$) δ174.03, 169.78, 157.05, 151.71, 140.08, 128.80, 128.71, 125.77, 115.93,112.36, 112.06, 69.96, 59.73, 54.95, 49.87, 44.24, 40.59, 38.03, 37.83, 35.61, 29.93, 27.19, 27.08, 18.72 15.79; MS (FD) m/z 481 (M+); $[\alpha]^{25}_{589}$ +57.23°, $[\alpha]^{25}_{365}$ +170° (MeOH, c=1.01); UV (MeOH) 274.4 nm (ε=2093), 202.8 nm.

Analysis for $C_{29}H_{40}N_2O_4$:
Calculated: C, 72.47; H, 8.39, N, 5.83.
Found: C, 72.49; H, 8.59; N, 5.63.

EXAMPLE 2

(αS,3R,4R)-4-(3-hydroxyphenyl)-3,4-dimethyl-α-(phenylmethyl)-1-piperidinepropanoic acid methyl ester hydrochloride A round bottom flask was purged with nitrogen and charged with THF (100 mL) and a 2.0 M solution of LDA (17.6 mL, 35.18 mmol, 2.05 equiv). The solution was cooled to −30° C. and the solution of a compound of Preparation 1 (15.24 g, 17.16 mmol, 1.0 equiv, 32.8 wt % in THF) was added over 20 minutes while maintaining the temperature between −26° and −28° C.

After stirring for 15 minutes at −25° C., benzyl bromide (5.81 g, 34.32 mmol, 2.0 equiv) was slowly added while maintaining the temperature between −17° and −20° C. The reaction mixture was stirred at −15° to −20° C. for three hours. ((αS,3R,4R)-4-(3-hydroxyphenyl)-3,4-dimethyl-α-(phenylmethyl)-1-piperidinepropanoic acid methyl ester/(αR,3R,4R)-4-(3-hydroxyphenyl)-3,4-dimethyl-1-piperidinepropanic acid methyl ester=97/3).

The reaction mixture was quenched with 1 N HCl (22 mL, 22 mmol). The pH was adjusted from 10.6 to 9.5 with 12 N HCl (2.3 mL) and the low temperature bath was removed. Heptane (50 mL) was added and the layers separated. Methanol (25 mL) was added to the organic layer and the solution cooled. Anhydrous HCl (1.3 g) was added to the solution while maintaining the temperature below 5° C. until the mixture was acidic. The hydrochloride salt precipitated during the addition. The mixture was concentrated to a net weight of 32.58 g. Methanol (36 mL) was then added to the oily concentrate and after a few minutes a precipitate formed. The mixture was stirred overnight at room temperature.

After cooling to 0° C. for 1.25 hours the precipitate was filtered, the flask rinsed with 10 mL of the filtrate, and the cake washed with cold methanol (10 mL). The solid was dried to give 2.93 g (40.9% yield) of a white powder.

Analysis by HPLC showed that the product was a 86:14 mixture of stereoisomers.

The crude hydrochloride salt (2.75 g) was added to methanol (13.75 mL) and the slurry heated at reflux for two hours. The mixture was cooled to about 0° C. The precipitate was filtered, the flask was rinsed with liltrate and the cake was washed with cold methanol (1.5 mL). The product was dried to yield 2.32 g of a white solid (84.4% yield).

Overall Yield: 34.5% (alkylation & hot reslurry)

Purity: 96.2% ((αS, 3R, 4R) -4-(3-hydroxyphenyl)-3,4-dimethyl-α- (phenylmethyl)-1-piperidinepropanoic acid methyl ester hydrochloride, 2.9% (αR, 3R, 4R)-4-(3-hydroxyphenyl)-3,4-dimethyl-(α-(phenylmethyl)-1-piperidinepropanoic acid methyl ester hydrochloride and 0.7% (αS, 3R, 4R)-4-(3-hydroxyphenyl)-3,4 -dimethyl-α-(phenylmethyl)-1-piperidinepropanoic acid monohydrate (HPLC area %). mp 230°–232 ° C. (dec), IR (KBr): 3174, 1732, 1620, 1586, 1276, 785,749, 706 $cm^{-1}$. $^1H$-NMR (DMSO-$d_6$): d [0.78 (d, 0.85 ×3H, J=7.2 Hz) & 1.02 (d, 0.15×3H, J=7.2 Hz), diastereomeric salts], [1.28 (s, 0.15×3H), 1.34 (s, 0.85×3H), diastereomeric salts], 1.76 (br d, 1H), 2.10–2.48 (m, 2H), 2.75–3.65 (m, 12H), 6.60–6.90 (m, 3H), 7.11 (t, 1H, J=7.8 Hz), 7.15–7.35 (m, 5H), 9.43 (br s, 1H), 9.75 (br s, 1H).

MS (FD): m/z 381 (100%, M-HCl).
Analysis for $C_{24}H_{32}ClNO_3$:
Calculate: C, 68.97; H, 7.72; N, 3.35; Cl,8.48.
Found: C, 69.27; H, 7.84; N, 3.42; Cl, 8.38.

EXAMPLE 3

(+)-((αS, 3R, 4R)-4-(3-hydroxyphenyl)-3,4-dimethyl-α-(phenylmethyl)-1-piperidinepropanoic acid monohydrate Deionized water (230 mL) was charged to a round bottom flask along with a 50% w/w sodium hydroxide solution (20.02 g, 250 mmol, 4.2 equiv). In one portion of the product of Example 2 (25.0 g, 60 mmol, 1 equiv) was added to the flask. The mixture was stirred at room temperature and filtered. The filter paper was rinsed with 33 mL of a 1 N sodium hydroxide solution. The solution was transferred to a round bottom flask suitable for a vacuum distillation. Methanol (240 mL) was charged to the solution. The pH of the solution was adjusted to 6.0 using concentrated hydrochloric acid (32.14 g). The methanol was removed at reduced pressure (100–200 mm Hg) and temperature (45°–50° C.). The methanol was removed until the weight of the concentrate was approximately 313 g. The slurry was allowed to stir for four hours. The pH of the solution was readjusted to 6.0 and the slurry was then cooled at 0°–5° C. for 1.5 hours. The desired product was filtered and washed three times with 50 mL of deionized water. The product was then dried. The desired monohydrate product was isolated as a white granular solid and weighed 21.3g for a 92% yield.

mp 178°–180 ° C. (dec.).

$^1$H NMR (300 MHz, DMSO) δ0.64 (d, 3H, J=6.9 Hz), 1.19 (s, 3H), 1.51 (d, 1H, J=13.1 Hz), 1.97–2.00 (m, 1H), 2.11 (td, 1H, J=3.6 Hz, 12.7 Hz), 2.34–2.95 (m, 9H), 6.54 (d, 1H, J=8.1 Hz), 6.66 (m, 2H), 7.06 (t, 1H, J=7.9 Hz), 7.14–7.28 (m, 5H), 9.22 (br s, 1H). $^{13}$C NMR (75.5 MHz, DMSO) δ15.5, 26.9, 29.5, 35.2, 37.5, 37.7, 42.7, 49.7, 53.7, 58.8, 112.2, 112.3,115.9, 126.0, 128.2, 128.7, 128.9, 139.4,151.2, 157.1, 175.1. UV (MeOH) λmax 203, ε17,860; 275, λ2356. MS (FD) m/z 368. IR (KBr) 3360, 3272, 2967, 1622, 1585, 1363, 844 cm$^{-1}$. $[\alpha]^{20}_{365}$ 304 (C 1.01, MeOH). KF=4.07% (Calcd for monohydrate: 4.70%).

Analysis for $C_{23}H_{31}NO_4$:

Calculated: C, 71.66; H, 8.10; N, 3.63.

Found: C, 72.29; H, 8.10; N, 3.71.

EXAMPLE 4

(2s, 3R, 4R)[[2-[[4-(3-hydroxyphenyl)-3,4-dimethyl-1-piperidinyl ]methyl]-1-oxo-3-phenylpropyl]-amino]acetic acid -methylpropyl ester sesquimalate salt (1:1.5 )

A compound of Example 1, (2.5 g, 5.2 mmol, 1.0 equiv) was dissolved in 50 mL of ethyl acetate. L-malic acid (1.03 g, 7.8 mmol, 1.5 eq) was added to the mixture. After the L-malic acid was dissolved by stirring, the solution was heated to 70° C. and 4.0 mL of acetone was added. The solution was crystallized. The product was isolated by filtration. The filter cake was washed with ethyl acetate. The salt was dried until the ethyl acetate levels were below 1%. The title compound was isolated as a white crystal. The sample was analyzed using x-ray powder diffraction. mp 94°–95OC.

IR (KBr) 3346.92, 2972.68, 1741.94, 1601.12 cm$^{-1}$;

$^1$H NMR (300 MHz, DMSO-d$_6$) δ9.70 (bs, 1H), 8.47 (t, 1H, J=1.9 Hz), 7.27–7.13 (m, 4H), 7.06 (t, 1H, J=7.9 Hz), 6.67 (d, 1H, J=8.0 Hz), 6.63 (s, 1H), 6.53 (dd, 1H, 8 Hz, J=1.7 Hz), 4.18 (t, 1.5H, J=5.8 Hz), 3.82–3.78 (m, 3H), 3.33–1.80 (m, 16 H), 1.48 (bd, 1H, J=13.0 Hz), 1.18 (s, 3H), 0.85 (d, 6H, J=6.7 Hz), 0.64 (d, 3H, J=6.9 Hz); $^{13}$C NMR (75.4 MHz, DMSO-d$_6$) δ175.63, 175.42, 171.44, 158.66, 138.63, 138.60, 130.50, 130.23,129.66, 128.02, 114.07, 114.05, 14.01, 113.94; MS (FD) m/z 481 (M+); UV (MeOH) 272.8 nm (e=797), 202.4 nm (ε=20576);

Analysis for $C_{70}H_{98}N_4O_{23}$:

Calculated: C, 61.65; H, 7.38; N, 4.10; O, 26.98.

Found: C, 61.40; H, 7.23; N, 4.1; O, 26.66.

EXAMPLE 5

(2S, 3R, 4R)[[2-[[4-(3-hydroxyphenyl)-3,4-dimethyl-1-piperidinyl ]methyl]-1-oxo-3-phenylpropyl]-amino]acetic acid dihydrate A solution of a compound of Example 1 (12.5 g, 0.026 mol, 1.0 equiv) in 315 mL of 3A ethanol was charged to round bottom flask. Water (74.0 mL) was added to the mixture. Aqueous solution of sodium hydroxide ((1.0 M) 0.077 mol, 3.0 equiv) was added dropwise over 10-15 minutes at 25°–30° C. The solution was stirred and then filtered. The pH of the solution was adjusted from 12.50 to 6.00 by addition of concentrated hydrochloric acid. The solution was seeded and (2S,3R,4R)[[2-[[4-(3-hydroxyphenyl)-3,4-dimethYl-1-piperidinyl]methyl]-1-oxo -3-phenylpropyl]amino]acetic acid began to precipitate within 10–15 minutes. The crystallization was stirred at 25° C. for two hours and then (2S,3R,4R)[[2-[[4-(3-hydroxyphenyl)-3,4-dimethYl-1-piperidinyl]methyl]-1-oxo -3-phenylpropyl]amino]acetic acid was filtered under slight suction to a wet cake. The crystals were slurried with 60 mL of water and filtered to a hard cake under suction. The crystals were dried to the dihydrate overnight (16 hours) under open air at 33% relative humidity at 25° C. by pulling air over the product in the filter funnel under slight suction. The title compound was isolated in 85% yield (10.2 g), from (αS,3R,4R)-4-(3-hydroxyphenyl)-3,4-dimethyl -α- (phenylmethyl)-1-piperidine propanoic acid monohydrate, as white crystals with a sharp melting point of 208° C. The sample was analyzed using x-ray powder diffraction.

IR (KBr) 3419, 3204, 3028, 1684, 1591 cm$^{-1}$;

$^1$H NMR (300 MHz, DMSO - d$_6$) δ9.18 (bs, 1H ), 8.34 ( t, 1H, J=5.5 Hz) 7.26–7.12 (m, 6H), 7.05 ( t, 1H, J=7.9 Hz ), 6.67 (d, 1H, J=8.0 Hz), 6.63 (s, 1H), 6.52 (dd, 1H, J=8.0 Hz, J=1.8 Hz), 3.65 (d, 2H, J=5.6 Hz), 2.89–2.10 (m, 14H), 1.91 (bd, 1H, J=6.7 Hz), 1.18 (s, 3H), 0.64 (d, 3H, J=6.9 Hz); $^{13}$C NMR (75.4 MHz, DMSO-d$_6$) δ173.54, 71.30, 157.05, 151.28, 139.83, 128.83, 128.73, 128.05, 125.82, 115.97, 112.14, 59.62, 54.59, 49.92, 43.75, 41.12, 39.95, 39.67, 39.39, 39.12, 38.84, 37.80, 37.73, 35.42, 29.68, 27.04, 15.54; MS (FD) m/z 425 (M+-2H$_2$O): UV (MeOH) 275.0 (ε=2246), 202.6 (ε=22709.4); $[\alpha]^{25}_{365}$=−1.18 (MeOH, c=1.0);

Analysis for $C_{25}H_{36}N_2O_6$:

Calculated: C, 65.20; H, 7.88; N, 6.08; O, 20.84.

Found: C, 64.96; H, 7.74; N, 6.10; O, 20.82;

EXAMPLE 6

(2S,3R,4R)[[2-[[4-(3-hydroxyphenyl)-3,4-dimethyl-1-piperidinyl]methyl]-1-oxo-3-phenylpropyl]-amino]acetic acid dihydrate Ethanol (2400 mL, 3A) and a compound of Example 4 (146 g with 5% EtOAc, 138.7 g pura, (0.203 mol, 1.0 equiv., 0.085 molal) were charged to a round bottom flask. A 1.0 M aqueous solution of sodium hydroxide (1200 mL, 1.2 mol, 5.9 equiv. ) was added dropwise over 20 minutes at 25°–30° C. The solution was stirred and then filtered. The pH of the solution was adjusted from 12.96 to 6.00 by addition of concentrated hydrochloric acid. The solution was seeded and (2S, 3R, 4R) [[2- [[4- (3-hydroxyphenyl) -3,4-dimethyl-1-piperidinyl]-methyl]-1-oxo-3-phenylpropyl]-amino]acetic acid began to precipitate within 10–15 minutes. The crystallization was stirred at 25° C. for two hours. The slurry was cooled to 0° C. and stirred. The (2S,3R,4R)[[2-[[4-(3-hydroxyphenyl) -3,4-dimethyl-1-piperidinyl]methyl]-1-oxo-3-phenylpropyl]amino]acetic acid product was filtered under slight suction to a wet cake. The crystals were slurried with 500 mL of 25° C. water with stirring, followed by slight suction, reslurried with 500 mL of water, and filtered to a hard cake under suction. The crystals were dried to the dihydrate overnight under open air at 35% relative humidity at 25° C. by pulling air over the product in the filter funnel under slight suction. The title compound was isolated in 93% (88 g) yield, as white crystals with a sharp melting point of 208° C.

Analysis for $C_{25}H_{36}N_2O_6$:
Calculated: C, 65.20; H, 7.88; N, 6.08; O,20.84.
Found: C, 65.38; H, 7.87; N, 6.25; O, 20.90;

EXAMPLE 7

(2S,3R,4R)[[2-[[4-(3-hydroxyphenyl)-3,4-dimethyl-1-piperidinyl]methyl]-1-oxo-3-phenylpropyl]-amino]acetic acid 2-methylpropyl ester hydrochloride aetone monosolvate A 6.0 g sample of a compound of Example 1 was dissolved in 60.0 mL of dry acetone. A 0.45 g portion of HCl gas (0.98 equiv.) dissolved in 30.0 mL of dry acetone was added dropwise at 25° C. The HCl gas in acetone was added dropwise until the pH was pH 3. When the pH reached 3, a second 1.0 mL aliquot of a compound of Example 1, at the same concentration as the starting solution, was added. Precipitate formed. The reaction was stirred at 25° C. for one hour and then cooled to 0° C. The reaction was stirred at 0° C. for two hours. The desired (2S,3R,4R)[[2-[[4-(3-hydroxyphenyl)-3,4-dimethyl-1-piperidinyl]methyl]-1-oxo-3-phenylpropyl]amino]acetic acid 2-methylpropyl ester hydrochloride salt was filtered with pressure filtration using nitrogen. The (2S, 3R, 4R)[[2-[[4-(3-hydroxyphenyl)-3,4-dimethyl-1-piperidinyl]methyl]-1-oxo-3-phenylpropyl]amino]acetic acid 2-methylpropyl ester hydrochloride salt was dried by streaming nitrogen over the liltrate to form the acetone monosolvate. The acetone monosolvate was characterized by capillary gas chromatographic analysis which showed 9.3%–9.97% (by weight) acetone. (Theoretical 10 percent). The product was characterized by removal of the acetone molecule of solvation.

The hydrochloride acetone monosolvate was dried further using a vacuum oven at 50° C. for 2 to 3 days. Formation of the hydrochloride monohydrate was affected by spreading the crystals over a large surface at 25° C. in 40% relative humidity for 2 days.

Yield was >85% with purity around 99.3% by reversed-phase HPLC.

mp 70°–75 ° C.; IR (KBr) 3217.7, 3063.4, 2965.0, 1749.7, 1671.5;

$^1$H NMR (300 MHz, DMSO-$d_6$) δ9.45 (bs, 1H), 9.37 (s, 1H), 8.94, (t, 0.85 H, J=1.5 Hz), 8.92 (t, 0.15H, J=1.5 Hz), 7.28–7.20 (m, H), 7.09 (t, 1H, J=7.8 Hz), 6.67–6.56 (m, 3H), 3.83–3.76 (m, 4H), 3.47–3.10 (m, 5H), 2.83 (dq, 2H, J=18.0 Hz, J=5.5 Hz, J=2.0 Hz), 2.7–2.0 m, 5H), 1.82 (sept, 1H, J=6.7 Hz ) 1.70 ( d, 1H, J=12.0 Hz ), 1.29 (s, 0.85 H), 1.24 (s, 0.15 H) 0.99 (d, 0.45 H, J=7.4 Hz), 0.85 (d, 6 H, J=6.6 Hz), 0.71 (d, 2.55 H, J=7.3 Hz); $^{13}$C NMR (75.4 Hz, DMSO-$d_6$) δ172.7, 169.8, 157.4, 149.4, 129.3, 128.3, 121.6, 118.6, 115.7, 112.9, 112.3, 53.9, 57.1, 70.2, 48.1, 46.4, 40.8, 37.3, 36.9, 27.3, 27.0, 26.5, 18.8, 15.1; UV (MeOH) 274 (ε=2738), 202.2 (ε=28413); MS (FD) 481 (M+-HCl-H2O);

Analysis for $C_{29}H_{41}N_2O_4 \cdot H_2O$:
Calculated: C, 65.09; H, 8.10; N, 5.23; O, 14.95; Cl, 6.63
Found: C, 65.06; H, 7.92; N, 5.27; O, 15.19; Cl, 6.92

EXAMPLE 8

(αS, 3R, 4R)-4-(3-hydroxyphenyl)-3,4-dimethyl-α-(phenylmethyl)-1-piperidinepropanoic acid ethyl ester hydrochloride A sample of (+)-3-(3,4-dimethyl-4-piperidinyl)-phenol (50.0 g, 243.5 mmol, 1.0 equivalent) was charged to a round bottom flask. Tetrahydrofuran (1 L) and ethyl acrylate (33.0 mL, 304.4 mmol, 1.25 equivalents) were added and the heterogeneous reaction mixture was stirred for several days at room temperature. The reaction mixture was filtered through diatomaceous earth and the transparent solution was stripped to a viscous amber oil weighing 75.0 g. A portion of the amino ester (1.16 g, 3.80 mmol, 1.0 equivalent) was redissolved in 10 mL of tetrahydrofuran (THF) and added to a −75 ° C. solution of lithium diisopropylamide (3.90 mL, 7.80 mmol, 2.05 equivalents) in THF (20 mL). The addition took approximately five minutes. The slurry was then stirred at −70 ° C. for 15 minutes and benzyl bromide (0.47 mL, 3.99 mmol, 1.05 equivalents) was added. The reaction was allowed to warm to −25° to −30 ° C. and stirred for 3 hours. The reaction was quenched with 10 mL of saturated ammonium chloride and 10 mL of H2O and 20 mL of ethyl acetate. The aqueous layer was separated. The organic layer was washed with saturated brine solution. The organic was then dried over MgSO4. The mixture was filtered and the resulting solution was then rotary evaporated to yield a yellow oil weighing 1.80 g. The mixture of product and starting material was then flash chromatographed with a mixture of ethyl acetate and hexane to isolate 1.07 g (71%) of the ethyl ester.

The ethyl ester from above (14.8 g, 37.4 mmol) was then dissolved in 150 mL of ethanol. Anhydrous hydrogen chloride was sparged into the solution and the ethanol was removed by rotary evaporation. The solid was then triturated with 50 mL of ethyl acetate and filtered. The solid was dried overnight at 30° C. to isolate 12.25 g of the hydrochloride (76%, melting point of 179°–181 ° C.). The diasteromer ratio was 49% αS, 3R, 4R (desired diastereomer) to 51% αR, 3R, 4R (undesired diastereomer).

The hydrochloride salt (1.02 g) was slurried in 5 mL of ethanol and refluxed for 3 hours. The mixture was allowed to cool back to room temperature and stirred. The mixture was stirred at 0° C. for 1 hour and then filtered. The salt was dried overnight at 40° C. The while solid isolated weighed 0.48 g (47%). The diastereomer ratio was 76% αS, 3R, 4R to 24% αR, 3R, 4R.

The hydrochloride sail (0.42 g) was slurried in 6 mL of ethanol and heated to reflux for 2 hours and then cooled back to room temperature and stirred. The slurry was cooled to 0° C. for 1 hour and filtered. The solid was dried wand 0.31 g (74%) of the salt was obtained. The diastereomer ratio was 92% αS, 3R, 4R to 8% αR, 3R, 4R.

A portion of the salt (0.24 g) was slurried a third time in 2.5 mL of ethanol. The mixture was healed at reflux for three hours and then allowed to cool back to room temperature and stirred. The slurry was cooled to 0° C. for 1 hour and then filtered. The solid was dried. The diastereomerically pure (98% αS, 3R, 4R) hydrochloride salt of the ethyl ester weighed 0.23 g (96%).

We claim:
1. A crystalline compound of the Formula 20

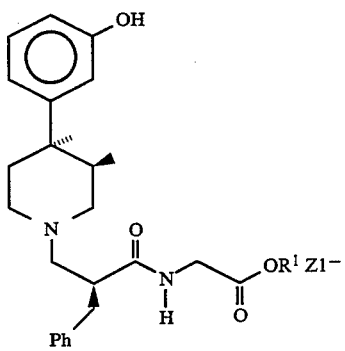

(20)

wherein R¹ is $C_1$-$C_6$ alkyl; Z1⁻ is selected from the group consisting of hydrochloride, malate, and sesquimalate;

wherein when Z1⁻ is sesquimalate then 3 molecules of malate are associated with 2 molecules of 20; and when Z1⁻ is hydrochloride then each molecule of 20 is solvated with one molecule of acetone.

2. A crystalline compound of claim 1 wherein Z1⁻ is hydrochloride.

3. A crystalline compound of claim 1 wherein Z1⁻ is sesquimalate.

4. A crystalline compound of claim 1 wherein the compound of Formula 1 is (2S, 3R, 4R)[[2-[[4-(3-hydroxyphenyl)-3,4-dimethyl-1-piperidinyl]methyl]-1-oxo-3-phenylpropyl]amino]acetic acid 2-methylpropyl ester.

5. A crystalline compound of claim 2 wherein the compound is (2S, 3R, 4R)[[2-[[4-(3-hydroxyphenyl)-3,4-dimethyl-1-piperidinyl]methyl]-1-oxo-3-phenylpropyl]-amino]acetic acid 2-methylpropyl ester hydrochloride acetone monosolvate.

6. A crystalline compound of claim 3 wherein the compound is (2S, 3R, 4R)[[2-[[4-(3-hydroxyphenyl)-3,4-dimethyl-1-piperidinyl]methyl]-1-oxo-3-phenylpropyl]-amino]acetic acid 2-methylpropyl ester.

7. A crystalline compound of claim 1 wherein the compound is (2S, 3R, 4R)[[2-[[4-(3-hydroxyphenyl)-3,4-dimethyl-1-piperidinyl]methyl]-1-oxo-3-phenylpropyl]-amino]acetic acid 2-methylpropyl ester malate.

8. A crystalline dihydrate compound of the Formula 5

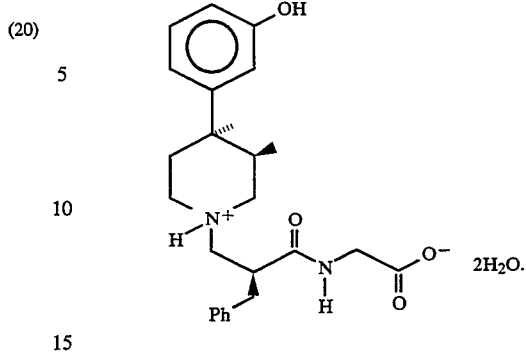

(5)

9. A compound of claim 8 wherein the crystalline dihydrate compound is at least 97% (2S,3R,4R)dihydrate.

10. A method for binding a peripheral opioid receptor in a patient which comprises administering to said patient an effective amount of a compound of claim 1.

11. A method for binding a peripheral opioid receptor in a patient which comprises administering to said patient an effective amount of a compound of claim 8.

12. A method for treating a condition selected from the group consisting of irritable bowel syndrome, idiopathic constipation, and non-ulcer dyspepsia; comprising administering an effective amount of a compound of claim 1.

13. A method for treating a condition selected from the group consisting of irritable bowel syndrome, idiopathic constipation, and non-ulcer dyspepsia; comprising administering an effective amount of a compound of claim 8.

14. A pharmaceutical formulation comprising an effective amount of a compound of claim 1 in combination with one or more pharmaceutically acceptable excipients.

15. A pharmaceutical formulation comprising an effective amount of a compound of claim 8 in combination with one or more pharmaceutically acceptable excipients.

16. A formulation of claim 15 wherein the formulation is a hard gelatin capsule.

17. A process for preparing a crystalline monohydrate compound of Formula 3

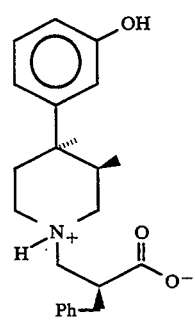

(3)

comprising the crystallization of 3 from a solvent comprised of about 50% methanol and about 50% water (by weight).

* * * * *